US006488954B1

United States Patent
Yoon et al.

(10) Patent No.: US 6,488,954 B1
(45) Date of Patent: Dec. 3, 2002

(54) LIQUID SUPPOSITORY COMPOSITION OF DICLOFENAC SODIUM

(75) Inventors: Sung June Yoon, Seoul (KR); Jei Man Ryu, Kyunggido (KR); Jae Hee Jung, Seoul (KR); Su Jin Cho, Seoul (KR)

(73) Assignee: Dong Wha Pharm. Ind. Co., Ltd. (KR)

( * ) Notice: Subject to any disclaimer, the term of this patent is extended or adjusted under 35 U.S.C. 154(b) by 0 days.

(21) Appl. No.: 09/938,797

(22) Filed: Aug. 24, 2001

Related U.S. Application Data

(63) Continuation of application No. PCT/KR00/00143, filed on Feb. 23, 2000.

(30) Foreign Application Priority Data

Feb. 24, 1999 (KR) ................................................ 99/6057

(51) Int. Cl.⁷ ............................. A61F 9/02; A61K 47/30
(52) U.S. Cl. ............................. 424/436; 424/DIG. 15; 514/772.3; 514/966
(58) Field of Search ..................... 424/436, DIG. 15; 514/966, 772.3

(56) References Cited

U.S. PATENT DOCUMENTS

| 4,946,870 A | 8/1990 | Partain, III et al. ......... 514/777 |
| 5,346,703 A | 9/1994 | Viegas et al. ............... 424/486 |

FOREIGN PATENT DOCUMENTS

| EP | 0 103 995 A2 | 3/1984 |
| EP | 0551626 A1 * | 7/1993 |
| WO | WO 94/03157 | 2/1994 |
| WO | WO 94/03186 | 2/1994 |
| WO | WO 97/30693 | 8/1997 |
| WO | WO 97/34580 | 9/1997 |

* cited by examiner

Primary Examiner—Carlos Azpuru
(74) Attorney, Agent, or Firm—Heslin Rothenberg Farley and Mesiti, P.C.; Candice J. Clement, Esq.

(57) ABSTRACT

The present invention relates to a liquid suppository composition comprising diclofenac sodium, poloxamer and at least one polymer select from the group consisting of polyethylene oxide and polyvinylpyrrolidone. The composition provides the advantages of. (1) a feel of foreign matter or discomfort does not occur when the composition is rectally administered; and (2) administration is easy and after rectal administration, the composition is neither leaked out from the anus nor shifted into the end of large intestine.

3 Claims, 3 Drawing Sheets

LIQUID SUPPOSITORY COMPOSITION OF DICLOFENAC SODIUM

CROSS REFERENCE TO RELATED APPLICATIONS

This application is a continuation of co-pending International Patent Application Number PCT/KR00/00143, filed Feb. 23, 2000, and claims priority from Korean Patent Application Number 1999/6057, filed Feb. 24, 1999. The entire disclosure of the prior applications are incorporated herein by reference.

TECHNICAL FIELD

The present invention relates to a liquid suppository composition of diclofenac sodium.

BACKGROUND ART

Diclofenac sodium, 2-[(2,6-dichlorophenyl)amino] benzeneacetic acid, monosodium salt, (Voltaren®, CibaGeneva Pharmaceuticals, Summit, N.J., USA) is one of the nonsteroidal anti-inflammatory agents with analgesic, antipyretic and anti-inflammatory properties. The potency of its antipyretic effect is similar to that of indomethacin, phenylbutazone and acetylsalicylic acid, while having the effect of uterine contraction, antihypertension and the treatment for menstrual disorder. Although oral-administered diclofenac sodium is almost completely absorbed, its typical adverse reactions in the gastrointestinal tract include gastric ulcer, GI hemorrhage and perforation. To avoid the various adverse reactions associated with the oral administration of diclofenac sodium, its suppository form was already introduced. However, the said suppository form has another disadvantages, that is not only the general disadvantages of the suppository form, but also adverse effects due to sudden increasing of blood concentration of drug after its administration and due to the inconveniency of twice medication per day.

These disadvantages can be eliminated by a formulation of the sustained-release dosage form in such a manner to combine some appropriate base with the materials that can make a drug to be sustained-released. However, such materials for sustained-releasing of drug are not dissolved in the oily bases by heating, while being in dispersed state. Thus it is necessary that the sustained-release dosage form should be prepared in such a manner that each component is homogeneously dispersed in oily bases. For example, there are several methods of preparing the sustained-release dosage form in the following manner:

- a method of changing the blending ratio of fatty acid ester (Japan Patent Pyung 2-73010, Pyung 1-11618, Pyung 7-138149, Sho 64-63512);
- a method of adding hydrogen lecithin to the base of conventional suppository with a very high melting point (Japan Patent Sho 63-14716); and,
- a method of adding polyglycerin fatty acid ester to the base of conventional suppository.

According to these methods, their drug application are limited due to the fact that the drug-release rate are controlled only by the contents of materials for sustained-release.

There is another method of controlling the drug-release rate by adding water-containing polymers to the conventional solid suppository [Drug Develop. and Ind. Pharm. 16(10), 1675-1686, 1990]. However, the rectal mucosa may be irritated during administration of the preparation formulated by using this method.

Likewise the conventional suppositories, the sustained-release dosage forms prepared by the said methods are applicable easily and widely to patients including elderly people and children, and the absorption of drug from those is not affected by meals, due to their special route of administration. But they have still encountered the following problems, likewise the conventional suppositories: (1) inconvenience in manufacture and handling; (2) a feel of foreign matter and discomfort on the part of patients during administration, and (3) greater deviation of bioavailability due to the drug absorption via the large intestine, not via rectum, due to the movement of the preparation Meantime, in recent years, there are many cases that poloxamer is selected as a base of suppository, because it is liquid at a low temperature but when temperature goes up, it can form gel. For example, a basic method of using poloxamer as a base for suppository composition is that the scope of gelation temperature of base is simply adjusted by modulating the concentrations of poloxamer and such poloxamer derivatives as Tetronic™(BASF Corp., Parsippany, N.J., USA), Tergitol™(Union Carbine, Danbury, Conn., USA), etc. (U.S. Pat. No. 4,188,373 and Canadian Patent 1,072,413). Another method of using poloxamer as a main base for suppository composition is that various kinds of additives are employed so as to adjust the gel strength and pH of suppository composition for applying it to the body cavity such as rectum, skin, etc. (U.S. Pat. No. 4,478,822, 4,474,951, 4,474,952, 4,474,752 and 4,474,753). However, since the said suppository compositions are in principle characterized by controlling the general properties of base only through the selection of proper poloxamer, their application to rectum are inappropriate; when these suppository compositions are administered to rectum, they are easily leaked out from the anus or shifted to the end of large intestine, thus a drug undergoes the first-pass effect.

In another method of using poloxamer for suppository composition, it is designed with the addition of polymers including carbomer to adjust the gelation temperature and gel strength that the composition can be applied to the body cavity such as skin, eye and rectum (Europe Patent Number 551626). Nevertheless, this composition has proven to be insufficient for its application to the suppository composition since the bioadhesive force and dissolution rate of the drug were not considered. Thereafter, another method of using sodium alginate, chitosan, etc., which are ionic polysaccharides, to be mixed with poloxamer has been disclosed so as to delivery drugs such as antipyretic to a body cavity (U.S. Pat. No. 5,346,703). However, this method has recognized some disadvantages in that (1) the physical properties of sodium alginate or chitosan is inappropriate to suppository form, (2) the irreversible base containing counter ion such as calcium ion ($Ca^{+2}$) is inconvenient in use and handling of suppository, (3) the scope of gelation temperature cannot be widely controlled due to its use of one poloxamer, and (4) the damages of rectal mucosa, which must be considered carefully during rectal administration, are severe.

Besides, another method of using chitosan as a main gel-forming material has been disclosed (U.S. Pat. No. 4,946,870 and EPPatent 103995). This method has also encountered some drawbacks in that (1) the accurate gel temperature of suppository composition cannot be made available, (2) although poloxamer is used, the composition contains some absorption enhancers, while concentrating on the application of peptide drugs only. There is another method of using polysaccharide as the main ingredient (International Patent WO94/03157 and WO94/03186), but this method has proven to be disadvantageous in that the accurate adjustment of physical properties such as gelation temperature and gel strength may not be easily available.

There is another method of using poloxamer, sodium alginate or chitosan as a base for application to a drug that is inadequate as an oral administration due to the hepatic first-pass effect, the severe gastrointestinal disturbance or the disintegration by gastric juice (International Patent WO97/30693 and WO97/34580). However, the base cannot be employed to diclofenac sodium of the present invention.

The suppository composition of this invention is characterized in that: (1) it has the suitable gelation temperature at 30–36° C. to be a liquid form at room temperature and readily becomes a gel at body temperature after rectal administration, (2) it has the gel strength of more then 15 sec with no weight, and is not leaked out the anus, (3) and it has suitable bioadhesive force of more then 50 dyne/cm$^2$ and does not move up to the end of the colon from the rectum, and does not give any damage to the rectal mucosa.

Therefore, an object of the present invention is to provide a novel liquid suppository composition containing diclofenac sodium, being characterized in that: (1) the process for manufacturing the composition is easy and economical, (2) the composition has better gel strength and bioadhesive force, (3) a feel of foreign matter or discomfort does not occur during rectal administration, (4) the administration of the composition is easy and (5) the composition is neither leaked out from the anus nor shifted into the end of large intestine.

DISCLOSURE OF THE INVENTION

The present invention relates to a liquid suppository composition comprising: a) 1–5 wt. % of diclofenac sodium; b) 25–40 wt. % of a solid-phase poloxamer mixture containing at least two poloxamers; and c) 0.1–1.0 wt. % of at least one polymer selected from the group consisting of polyethylene oxide and polyvinylpyrrolidone.

Poloxamer, a copolymer of polyethylene-propylene glycol, is a liquid at low temperature but forms a gel at high temperature. According to the present invention, a variety of poloxamer mixtures can be used. The detailed examples of solid-phase poloxamer include poloxamer 407, poloxamer 338, poloxamer 288, poloxamer 238 and poloxamer 188; among them, it is preferred to select the solid-phase poloxamer 407 since it can form gel, at a very low concentration of 20%, at room temperature and is non-toxic. By using the mixture of poloxamer 407 and other poloxamers, the appropriate scope of gelation temperature can be adjusted easily. In particular, in case of the poloxamer mixture containing poloxamer 407 and poloxamer 188 in a certain weight ratio, the gelation temperature in the range of 30–36° C., of which range is proper, can be adjusted easily. Hence, it is preferred that the weight ratio of both poloxamer 407 and poloxamer 188 is 1: 1–1.5, while the amount of the poloxamer mixture is preferably added in the range of 25–40 wt. % to the total composition for rectal administration. If the amount of the poloxamer mixture is less than 25 wt. %, the gel strength and bioadhesive force are weak, but in case of exceeding 40 wt. %, a higher degree of viscosity makes it difficult to prepare the desired product.

To improve the gel strength and bioadhesive force of suppository during manufacture, various types of the following polymers have been commonly applied in the past: acrylic polymers such as carbopol and polycarbophil; cellulose-based polymers such as hydroxypropyl cellulose and hydroxypropylmethyl cellulose; or, natural polymers such as sodium alginate and chitosan. However, these polymers showing the coagulation in diclofenac sodium solution are inappropriate to the composition of the present invention.

By contrast, these hydrophilic polymers such as polyethylene oxide and polyvinylpyrrolidone can be used as a polymer contained in the liquid suppository composition of the present invention, since they are well mixed with poloxamer and diclofenac sodium to form a clear, transparent, and viscous solution. This reflects that since these hydrophilic polymers may react with hydroxyl group (—OH) of poloxamer, carboxyl group (—COOH) or amino group (—NH) of diclofenac sodium to form a hydrogen bond, more strong three-dimensional net-working structure of poloxamer may be formed. It seems that because these polymers can form the strong hydrogen bond with oligosaccharide groups of rectal mucosa, very small amount of these polymers can serve to enhance the gel strength and bioadhesive force.

Further, since the viscosity of the composition may vary depending on the molecular weight of polymer added and its content, the liquid suppository composition with proper bioadhesive force and gel strength for therapeutic use can be prepared by the appropriate adjustment of its molecular weight and content. The dissolution rate of drug can be also controlled to be proper for therapeutic use. Preferably, at least one polymer selected from the group consisting of polyethylene oxide and polyvinylpyrrolidone is added to the total composition in a weight ratio of about 0.1–1.0 wt. %, more preferably in a weight ratio of 0.3–1.0 wt. %. If the content of polymer is less than 0.1 wt. % to the total composition, its gel strength and bioadhesive force cannot be properly controlled, and where it exceeds 1.0 wt. %, a higher viscosity makes it difficult to manufacture the desired product.

Polyethylene oxide with the molecular weight of $1 \times 10^5 - 9 \times 10^5$ can be used. The molecular weight of polyvinylpyrrolidone may vary, although 630,000, is the most preferred. If these molecular weights are small, the viscosity of final product becomes reduced and vice versa. The dosage form for rectal composition can be designed by using appropriate molecular weight, as needed.

In addition to diclofenac sodium, poloxamer, and polyethylene oxide and/or polyvinylpyrrolidone, the liquid suppository composition of the present invention may also include one or more of the following common additives used for the conventional dosage forms of rectal administration: preservatives (e.g., sodium benzoate, potassium sorbate, parabens, etc.), pH modulator (e.g., hydrochloric acid, citric acid, sodium hydroxide, etc.), and stabilizer (e.g., methionine, etc.).

BEST MODE FOR CARRYING OUT THE INVENTION

Figure 1:
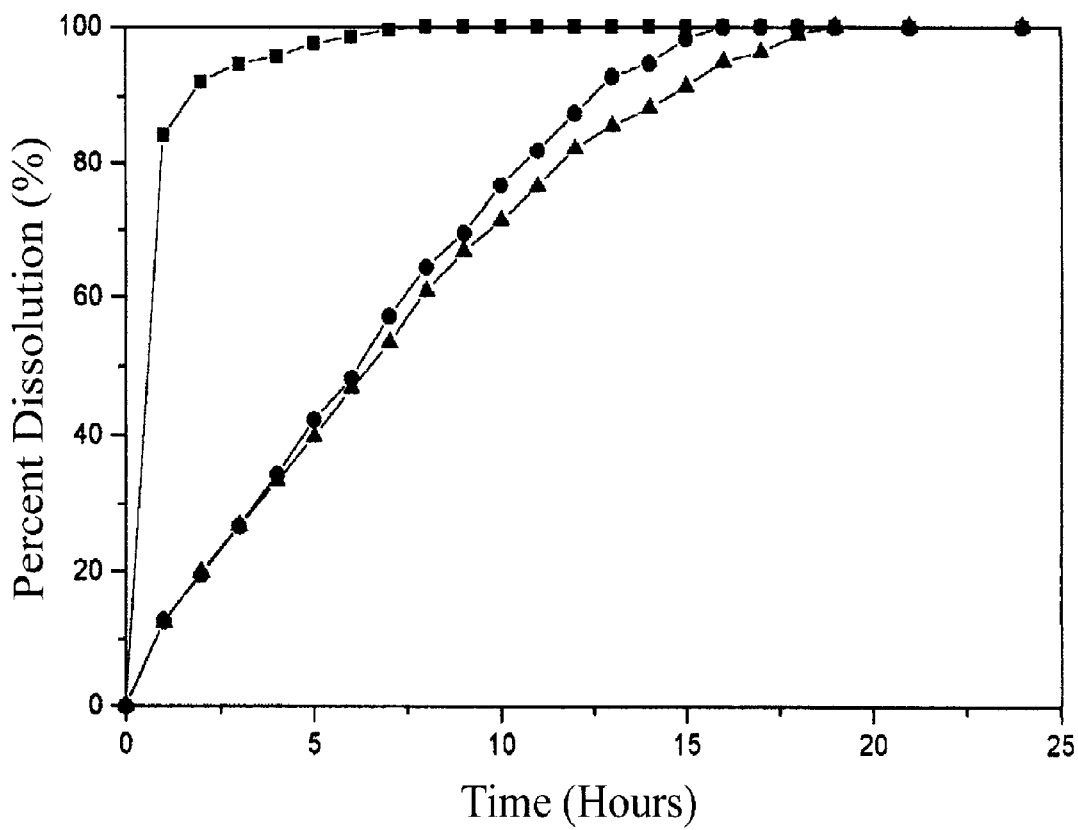
FIG. 1 shows the dissolution profiles of the compositions of Example 2 (●) and Example 3 (▲), and a conventional suppository (■) of diclofenac suppository.

The present invention is described with reference to Examples in more detail. However, it should be noted that the present invention is not restricted to those examples.

EXAMPLE 1–8

According to the blending ratio shown in Table 1, suppository compositions comprising sodium diclofenac were prepared. At first, poloxamer and other polymers were dissolved in water and then, drug and other components were successively added to the mixture for dissolving completely. Then, water was added to be a total of 100 g in the weight of this mixture and the suppository composition was finally prepared.

Comparative Example 1–8

Substituting acrylic polymer, cellulose polymer or natural polymer for polyethylene oxide and polyvinylpyrrolidone in Example 1–8, suppository compositions were prepared. The blending ratio is shown in Table 2.

Comparative Example 9–16

Except that polyethylene oxide and polyvinyl pyrrolidone were not added, suppository compositions were prepared by the same blending ratio and the same process as those of Example 1–8.

Comparative Example 17–20

With the blending ratio shown in Table 3, suppository compositions were prepared by the same process as that of Example 1–8.

TABLE 3

(Unit: g)

| Components | Comparative Example | | | |
|---|---|---|---|---|
| | 17 | 18 | 19 | 20 |
| Poloxamer 407 | 15 | 15 | 9 | 19 |
| Poloxamer 188 | 18 | 19 | 9 | 23 |
| Polyethylene oxide (M.W = 3 × $10^5$) | 0.01 | 1.5 | 0.3 | 0.3 |
| Diclofenac sodium | 2 | 2 | 2 | 2 |
| Methylparaben | 0.06 | | 0.05 | |
| Propylparaben | 0.02 | | 0.04 | |
| Sodium benzoate | | 0.1 | | 0.1 |
| Water | q.s. | q.s. | q.s. | q.s. |
| Total amount (g) | 100 | 100 | 100 | 100 |

The suppository compositions of Examples 1–8 were clear, transparent and viscous, while those of Comparative examples 1–8 were not prepared properly due to occurrence of coagulation during the preparation. In other words, it was found out that acrylic polymers such as carbopol and polycarbophil, cellulose polymers such as hydroxypropylmethylcellulose, and natural polymers such

TABLE 1

(Unit: g)

| Components | Example | | | | | | | |
|---|---|---|---|---|---|---|---|---|
| | 1 | 2 | 3 | 4 | 5 | 6 | 7 | 8 |
| Poloxamer 407 | 15 | 15 | 15 | 17 | 12 | 14 | 16 | 13 |
| Poloxamer 188 | 18 | 19 | 19 | 19 | 18 | 18 | 20 | 17 |
| Polyethylene oxide (MW = 3 × $10^5$) | 0.1 | 0.3 | | | | | 0.2 | |
| Polyethylene oxide (MW = 9 × $10^5$) | | | 0.3 | | 0.6 | 0.5 | | |
| Polyvinylpyrrolidone | | | | 1.0 | | | | 0.7 |
| Diclofenac sodium | 2 | 2 | 2 | 2 | 2 | 2 | 2 | 2 |
| Methylparaben | 0.06 | | 0.06 | | 0.05 | | 0.07 | 0.06 |
| Propylparaben | 0.02 | | 0.03 | | 0.05 | | 0.03 | 0.04 |
| Sodium benzoate | | 0.1 | | 0.1 | | 0.1 | | |
| Water | q.s. | q.s. | q.s. | q.s. | q.s. | q.s. | q.s. | q.s. |
| Total amount (g) | 100 | 100 | 100 | 100 | 100 | 100 | 100 | 100 |

TABLE 2

(Unit: g)

| Components | Comparative Example | | | | | | | |
|---|---|---|---|---|---|---|---|---|
| | 1 | 2 | 3 | 4 | 5 | 6 | 7 | 8 |
| Poloxamer 407 | 15 | 15 | 15 | 17 | 12 | 14 | 16 | 13 |
| Poloxamer 188 | 18 | 19 | 19 | 19 | 18 | 18 | 20 | 17 |
| Polycarbophil | | 0.3 | | | | | | 0.7 |
| Carbopol | | | 0.3 | | | | | |
| Hydroxypropylmethyl cellulose | | | | 1.0 | | | 0.2 | |
| Sodium alginate | 0.1 | | | | | 0.5 | | |
| Chitosan | | | | | 0.6 | | | |
| Diclofenac sodium | 2 | 2 | 2 | 2 | 2 | 2 | 2 | 2 |
| Methylparaben | 0.06 | | 0.06 | | 0.05 | | 0.07 | 0.06 |
| Propylparaben | 0.02 | | 0.03 | | 0.05 | | 0.03 | 0.04 |
| Sodium benzoate | | 0.1 | | 0.1 | | 0.1 | | |
| Water | q.s. | q.s. | q.s. | q.s. | q.s. | q.s. | q.s. | q.s. |
| Total amount (g) | 100 | 100 | 100 | 100 | 100 | 100 | 100 | 100 | as sodium alginate and chitosan are not suitable for the composition of the present invention since they were coagulated with diclofenac sodium.

Efficacy tests on the suppository compositions of Examples and Comparative examples were performed by means of the following Experimental examples.

Experimental Example 1

Measurement of Gelation Temperature

About 10 g of sample of each suppository composition prepared from Examples and Comparative examples was charged into a 20 ml container with a magnetic bar and the container was fitted in a water bath at 4° C. A digital thermometer was put into the sample not to be contact with the magnetic bar, and the sample was stirred at a constant rate. With increasing the temperature at a rate of 1° C./min, the gelation temperature was determined as the temperature of the point that the magnetic bar was completely stopped (Miyazaki, S., Nakamura, T., Takada, M., 1991. Thermosensitive sol-gel transition of Pluronic F-127, *Yakuzaigaku* 51, 36–43). The results are shown in Table 4.

Experimental Example 2

Measurement of Gel Strength 50 g of sample of each suppository composition prepared from Examples and Comparative examples was charged into a 100 ml mass cylinder, and equilibrated in a water bath at 36.5° C. for 30 minutes. After placing a gel strength device on the mass cylinder, the time (sec) that the device went down was measured (Schmolka, I.R., 1972, Artificial skin I. Preparation and properties of Pluronic F-127 gels for treatment of burns, *J Biomed. mater.* Res. 6, 571–582). The results are shown in Table 4.

Experimental Example 3

Measurement of Bioadhesive Force

Rectal mucosa of a rabbit was attached to two vials of a bioadhesive force device, and a proper amount of the composition was put between them. With piling up counterpoises on the device by turns, the bioadhesive force was determined as the weight of counterpoises of the time when the vials were dropped (H -G Choi, J -H Jung, J -M Ryu, S -J-Yoon, Y -K Oh and C -K Kim, 1998, Development of in situ-gelling and mucoadhesive acetaminophen liquid suppository, *Int. J. Pharm.*, 165, 33–44). The results are shown in Table 4.

Experimental Example 4

Test on Leakage of the Composition From the Anus

The suppository composition was inserted into the anus of a rabbit in 5 cm depth using a stomach sonde needle for rats, and the rabbit was diagonally placed with an inclination of 45 degrees. After the rabbit was observed for 30 minutes, it was determined as acceptable when the suppository composition was not leaking out from the anus. The results are also shown in Table 4.

TABLE 4

| | Gelation Temp (° C.) | Gel strength (sec) | Bioadhesive Force (dyne/cm$^2$) × 10$^2$ | Leakage of composition from the anus |
|---|---|---|---|---|
| Example 1 | 34 | 27.2 | 140 | acceptable |
| Comparative Example 9 | 39 | 3.4 | 8.7 | leakage |
| Example 2 | 33 | 34.7 | 347 | acceptable |
| Comparative Example 10 | 38 | 5.6 | 12.5 | leakage |
| Example 3 | 33 | 37.1 | 620 | acceptable |
| Comparative Example 11 | 37 | 7.8 | 17.2 | leakage |
| Example 4 | 33 | 28.3 | 117 | acceptable |
| Comparative Example 12 | 36 | 9.2 | 25.8 | leakage |
| Comparative Example 17 | 337 | 11.2 | not measured | leakage |
| Comparative Example 18 | 30 | not measured | not measured | — |
| Comparative Example 19 | no gelation | not measured | not measured | — |
| Comparative Example 20 | 20 | not measured | not measured | — |

As shown in Table 4 above, gelation temperature of the suppository compositions of the present invention (Examples 1–4) was 33–34° C., which was 3–5° C. lower than 36–39° C., gelation temperature of the compositions of Comparative examples 9–12. In addition, gel strength and bioadhesive force of the compositions of the present invention were 3–8 times and 4 times higher than those of Comparative examples, respectively. As shown in the results above, the suppository compositions of the present invention were superior in that they had properly lower gelation temperature, higher gel strength, more excellent bioadhesive force and less of leakage from the anus than the compositions of Comparative examples 9–12 devoid of polyethylene oxide or polyvinylpyrrolidone.

Furthermore, the composition of Comparative example 17 showed high gelation temperature and too low gel strength, and leaked out very easily from the anus. The compositions of Comparative example 18–20 showed too low gel strength or did not form gel, and it was impossible to measure their gel strength and bioadhesive force.

Experimental Example 5

Dissolution Test

The suppository compositions of Example 2 and 3 were put in a semi-permeable membrane and both sides thereof were tied up with threads. Elution test was performed in phosphate buffer solution of pH 6.7 at 100 rpm, and the solution was sampled and analyzed at 1-hour interval. The compositions of the present invention were found out to have a sustained-release tendency, from the results of comparing the dissolution profile of a conventional suppository of diclofenac sodium with that of the compositions of the present invention (See FIG. 1).

Experimental Example 6

Damage Test on Mucosal Membrane

The suppository compositions (Example 2 and 3) according to the present invention and a conventional suppository of sodium diclofenac were inserted into the anus of rabbits in 5 cm depth using a stomach sonde needle for rats. After 6 hours, the rectum was isolate, rinsed with a saline solution, fixed in 10% neutral carbonate-buffered formaldehyde, embedded in paraffin using an embedding center and cut into slices. The slices were stained with hematoxylin-eosin for microscopic analysis. The changes of rectal mucosa were evaluated as Types I, II and III (A. S. Reid, et. al., *Int. J Pharm.*, 40, 181 (1987)).

Figure 2A:
FIGS. 2a and 2b are photomicrographs of rectal mucosa prior to administration of a suppository composition of the present invention and 6 hours post administration
Figure 2B:
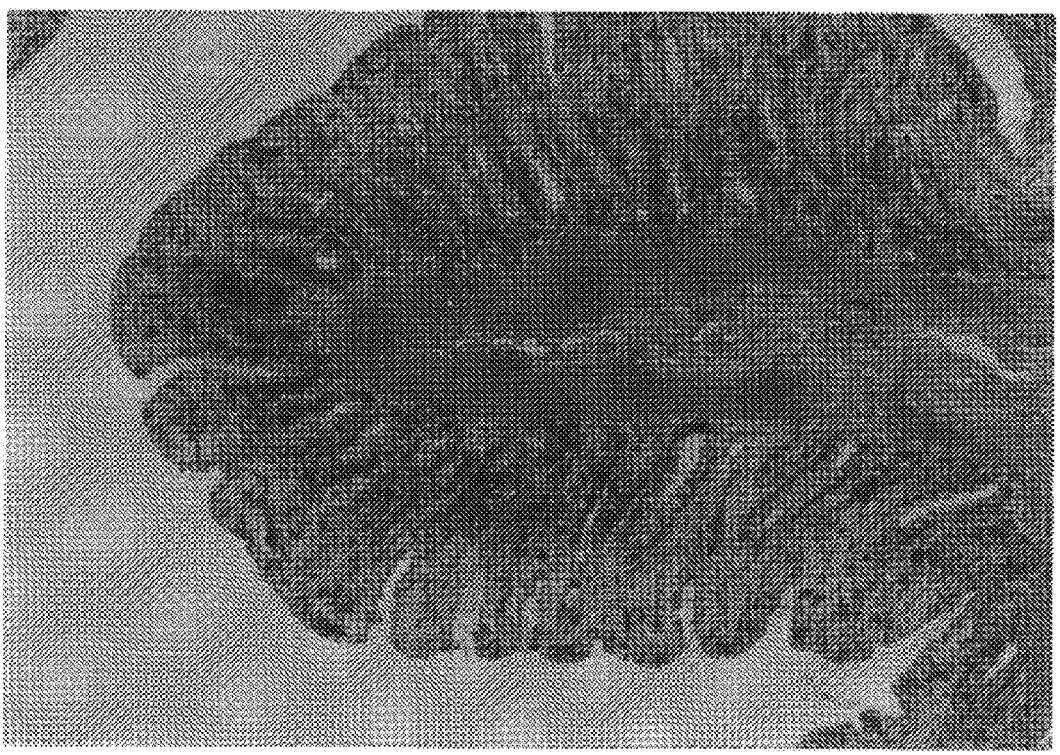

As a result, it was found out that the rectal mucosa administered with the conventional suppository of diclofenac sodium was damaged 2-3 times more than that of compositions of Example 2 and 3, on the basis of Type III determined as the most damaged in rectal mucosa (See Table 5). None of damage was found when rectal mucosa (FIG. 2b) of 6 hours after insertion of the composition of Example 2 into the rectum, was compared with rectal mucosa (FIG. 2a) before insertion.

TABLE 5

Percentage of damage of rectal mucosa by the type (unit: %)

| Classification | Number of animals in experiments (N) | Change of rectal mucosa | | |
|---|---|---|---|---|
| | | Type I[a] | Type II[b] | Type III[c] |
| Control group* | 1 | 5.0 | 4.5 | 0.5 |
| Reference group** | 5 | 5.8 ± 0.60 | 10.4 ± 1.22 | 7.5 ± 3.96 |
| Example 2 | 5 | 5.0 ± 0.45 | 9.1 ± 1.81 | 2.8 ± 1.09 |
| Example 3 | 5 | 6.1 ± 0.57 | 9.2 ± 2.04 | 3.5 ± 2.22 |

*Control group: without administration
** Reference group: conventional suppository of diclofenac sodium
[a] Type I: state in which some epithelial cells have detached and some continue to detach from the mucosa
[b] Type II: state that height of epithelial cells have become low on the whole
[c] Type III: state that epithelial cells have been completely detached from mucosa, and a mucosa has been exposed Experimental Example 7

Test to Identify the Location of Composition in the Rectum

The suppository composition containing 0.1% of a Blue Number 1 Lake staining agent additionally was inserted into the anus of rats in 5 cm depth using a stomach sonde needle for a rat. The rectum was sectioned from the body after 5 minutes and from another rats after 4 hours, and the location of the suppository composition in the rectum was identified. It was found out that the suppository composition was not moved to the terminal rectum not only after 5 minutes but also after 4 hours.

As noted in the above test results, the rectal composition of the present invention is quite effective in terms of (1) excellent physiochemical properties such as gelation temperature, gel strength, bioadhesive force and retention time of the composition at the administered site, (2) significant reduction of damages in rectal mucosa, and (3) excellent sustained release property of the drug from the composition without being shifted into the end of large intestine.

We claim:

1. A liquid suppository composition comprising:
   a) 1–5 wt. % of diclofenac sodium;
   b) 25–40 wt. % of a solid-phase poloxamer mixture, the mixture containing at least two poloxamers; and
   c) 0.1–1.0 wt. % of at least one polymer selected from the group consisting of polyethylene oxide and polyvinylpyrrolidone.

2. The liquid suppository composition according to claim 1, wherein the solid-phase poloxamer mixture consists of poloxamer 407 and poloxamer 188.

3. The liquid suppository composition according to claim 2, wherein the weight ratio of both poloxamer 407 and poloxamer 188 is 1:1–1.5.

* * * * *